(12) United States Patent
Mueting et al.

(10) Patent No.: US 9,861,580 B2
(45) Date of Patent: Jan. 9, 2018

(54) METHOD OF MAKING A DRY POWDER PHARMACEUTICAL COMPOSITION

(75) Inventors: Michael W. Mueting, Stillwater, MN (US); Daniel C. Duan, St. Paul, MN (US); Stephen W. Stein, Lino Lakes, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 1156 days.

(21) Appl. No.: 13/001,630

(22) PCT Filed: Jun. 22, 2009

(86) PCT No.: PCT/US2009/048099
§ 371 (c)(1),
(2), (4) Date: Dec. 28, 2010

(87) PCT Pub. No.: WO2010/002613
PCT Pub. Date: Jan. 7, 2010

(65) Prior Publication Data
US 2011/0104362 A1 May 5, 2011

Related U.S. Application Data

(60) Provisional application No. 61/077,746, filed on Jul. 2, 2008.

(51) Int. Cl.
| *B05D 1/28* | (2006.01) |
| *A61K 9/14* | (2006.01) |
| *A61K 9/00* | (2006.01) |
| *A61K 31/137* | (2006.01) |

(52) U.S. Cl.
CPC ............ *A61K 9/143* (2013.01); *A61K 9/0075* (2013.01); *A61K 31/137* (2013.01); *A61K 9/146* (2013.01)

(58) Field of Classification Search
CPC ................................. B05D 1/28; A61K 9/2893
USPC .................... 427/2.14; 424/452, 489, 490
See application file for complete search history.

(56) References Cited

U.S. PATENT DOCUMENTS

| 2,801,185 | A |   | 7/1957  | Iler |   |
|-----------|---|---|---------|------|---|
| 4,455,205 | A |   | 6/1984  | Olson et al. | |
| 4,478,876 | A |   | 10/1984 | Chung | |
| 4,486,504 | A |   | 12/1984 | Chung | |
| 4,491,508 | A |   | 1/1985  | Olson et al. | |
| 4,522,958 | A |   | 6/1985  | Das et al. | |
| 4,767,726 | A | * | 8/1988  | Marshall ............... C03C 11/002 501/32 |
| 5,037,579 | A |   | 8/1991  | Matchett | |
| 5,258,225 | A |   | 11/1993 | Katsamberis | |
| 5,443,603 | A | * | 8/1995  | Kirkendall ....................... 51/296 |
| 6,051,252 | A |   | 4/2000  | Liebowitz et al. | |
| 6,153,224 | A |   | 11/2000 | Staniforth | |
| 6,329,058 | B1 |  | 12/2001 | Arney et al. | |
| 6,432,526 | B1 |  | 8/2002  | Arney et al. | |
| 6,811,096 | B2 |  | 11/2004 | Frazier et al. | |
| 7,189,768 | B2 |  | 3/2007  | Baran, Jr. et al. | |
| 2003/0102099 | A1 | | 6/2003 | Yadav et al. | |
| 2004/0170822 | A1 | * | 9/2004 | Rohrbaugh ............. B08B 3/026 428/323 |
| 2005/0113489 | A1 | | 5/2005 | Baran, Jr. et al. | |
| 2005/0196345 | A1 | | 9/2005 | Diederichs et al. | |
| 2005/0228075 | A1 | * | 10/2005 | Gogos ................. C06B 21/0025 523/220 |
| 2005/0238804 | A1 | | 10/2005 | Garbar et al. | |
| 2007/0120281 | A1 | * | 5/2007 | Khusid ..................... B01J 2/006 264/11 |
| 2007/0178165 | A1 | * | 8/2007 | Altreuter .............. A61K 9/0019 424/499 |
| 2007/0212542 | A1 | | 9/2007 | Guo et al. | |
| 2008/0166500 | A1 | * | 7/2008 | Byeon ................. C23C 18/1837 427/576 |
| 2008/0286278 | A1 | * | 11/2008 | Connelly ............... C07K 16/00 424/140.1 |
| 2010/0266697 | A1 | | 10/2010 | Dunbar | |

FOREIGN PATENT DOCUMENTS

| WO | WO 02/00197 | 1/2002 |
| WO | WO 02/43700 | 6/2002 |
| WO | WO 2007/019229 | 2/2007 |
| WO | WO 2007019229 A1 * | 2/2007 |
| WO | WO 2007/117681 | 10/2007 |
| WO | WO 2008/002568 | 1/2008 |
| WO | WO 2009/142852 | 11/2009 |

OTHER PUBLICATIONS

Ben-Jebria et al., Inhalation System for Pulmonary Aerosol Drug Delivery in Rodents Using Large Porous Particles, Aerosol Science and Technology 32:421] 433 (2000).*
Linsenbuhler, M., et al., "An innovative dry powder coating process in non-polar liquids producing tailor-made micro-particles," *Powder Technology*, 158, 2003, pp. 3-20.
Kawashima, Y., et al., Design of inhalation dry powder of pranlukast hydrate to improve dispersibility by the surface modification with light anhydrous silicic acid (Aerosil 200), *Int'l Journal of Pharmaceutics*, 173, 1998, pp. 243-251.
Li J. et al., "Visualization and Characterization of Poly(amidoamine) Dendrimers by Atomic Force Microscopy," *Langmuir 2000*, 16, 5613-5616.

(Continued)

*Primary Examiner* — Dah-Wei D Yuan
*Assistant Examiner* — Hai Yan Zhang

(57) ABSTRACT

A method of making active pharmaceutical ingredient particles with surface-modified nanoparticles deposited on the particles' surfaces, the method comprising: providing a plurality of media particles having surfaces with the surface-modified nanoparticles deposited on the surfaces; mixing the plurality of media particles with the active ingredient particles, both of which are in dry form, to provide active ingredient particles having surfaces with the surface-modified nanoparticles deposited on the surfaces; and separating the plurality of media particles from the active ingredient particles having surfaces with the surface-modified nanoparticles deposited on the surfaces is disclosed.

20 Claims, No Drawings

(56) References Cited

OTHER PUBLICATIONS

Sastre et al., "On the Incorporation of Buckminsterfullerence $C_{60}$ in the Supercages of Zeolite Y," *J. Phys. Chem.* B 1997, 101, 10184-10190.
Binks, B.P. et al., "Phase Inversion of particle-stabilized materials from foams to dry water," *Nature Materials*, vol. 5, Nov. 2006, 865-869.

* cited by examiner

METHOD OF MAKING A DRY POWDER PHARMACEUTICAL COMPOSITION

CROSS REFERENCE TO RELATED APPLICATIONS

This application is a national stage filing under 35 U.S.C. 371 of PCT/US2009/048099, filed Jun. 22, 2009, which claims priority to U.S. Provisional Application No. 61/077,746, filed Jul. 2, 2008, the disclosure of which is incorporated by reference in its/their entirety herein.

BACKGROUND

The preparation or delivery of pharmaceutical drugs and medicaments as powders is demanding. Pharmaceutical applications must take careful account of various particle or powder characteristics, and pharmaceutical compositions often are prepared as powders as an intermediate step to final formulation in many forms for delivery to the patient. Pharmaceutical compositions can be tableted or encapsulated for oral gastro-intestinal ingestion and delivery. Powder pharmaceutical compositions also can be incorporated into a dry powder inhaler (DPI) for delivery to the respiratory tract. Dry powder inhalation of a pharmaceutical composition requires unique and challenging physical property profiles for a powder. For efficient and efficacious delivery to the lung in powder form, drug particles must be sufficiently small and deagglomerated. Lung deposition improves substantially for particles less than 5 microns in aerodynamic diameter and decreases substantially for particles with an aerodynamic diameter greater than 5 microns. However, below 5 microns in particle diameter, deagglomeration efficiency declines markedly.

Balancing these competing effects, in one example, has involved adsorbing small respirable drug particles onto larger inert carrier particles which provide for bulk deagglomeration but which require additional energy to release the drug from the surface of the carrier particles. Recent advances in improving the flowability characteristics of powders by adding surface-modified nanoparticles are disclosed in International Publication No. WO 2007/019229, entitled "Compositions Exhibiting Improved Flowability" (incorporated herein by reference). However, challenges remain in handling surface-modified nanoparticles and pharmaceutically active ingredients.

There is, therefore, a continuing need for methods of making pharmaceutical compositions in dry powder form.

SUMMARY

It has now been found that surface-modified nanoparticles can be effectively applied to a micronized active pharmaceutical ingredient by mixing the active ingredient with media particles having surfaces with the surface-modified nanoparticles deposited on the surfaces and then separating the media particles from the active ingredient. The media particles are selected such that they can be separated from the active ingredient, and in certain embodiments, such that when separated they leave essentially no fragments of the media particles with the active ingredient. After the mixing and separating, the resulting active ingredient particles have a portion of the surface-modified nanoparticles, previously on the media particles, now deposited on the active ingredient particles' surfaces. The active ingredient particles, thereby, have significantly improved flowability and dispersibility characteristics and, in certain embodiments, can be used in dry powder inhalers (DPIs). In certain embodiments, the mixing is carried out in dry form, with no liquid which could adversely affect the active ingredient or which must be removed by evaporation, sublimation, or the like.

Accordingly, there is provided a method of making active pharmaceutical ingredient particles having surfaces with surface-modified nanoparticles deposited on the surfaces, the method comprising:

providing a plurality of media particles having surfaces with surface-modified nanoparticles deposited on the surfaces;

mixing the plurality of media particles with active ingredient particles to provide the active ingredient particles having surfaces with a portion of the surface-modified nanoparticles deposited on the surfaces; and separating the plurality of media particles from the active ingredient particles having surfaces with the portion of the surface-modified nanoparticles deposited on the surfaces;

wherein the media particles have at least one feature which is sufficiently different from at least one feature of the active ingredient that the media particles can be separated from the active ingredient particles.

The surface-modified nanoparticles may have a hydrophilic or hydrophobic surface modification. Examples of core materials for the nanoparticles include silicas, titania, iron oxides, zinc oxides, alumina, metal phosphates such as a calcium phosphate, metal sulfates, metal chlorides, and combinations thereof. For certain embodiments, the mean diameter of the nanoparticles may be 20 nm or less.

The active ingredient particles, in certain embodiments, have a mean physical particle diameter of 100 micrometers or less, or less than 10 micrometers. The diameter of these particles, however, is substantially larger than the diameter of the nanoparticles, for example, at least 10 to 1000 times larger.

The media particles as compared to the active ingredient particles can be larger, more dense, more attracted to a magnetic field, or can have one or more other features or combinations thereof useful for separating the media particles from the active ingredient particles.

Definitions

The term "nanoparticle" as used herein refers to particles, groups of particles, particulate molecules (i.e., small individual groups or loosely associated groups of molecules) and groups of particulate molecules that while potentially varied in specific geometric shape have an effective, average, or mean diameter of less than 100 nanometers. For certain embodiment, the mean diameter is at least 1 nanometer. For certain embodiments, the mean diameter is at least 2 nanometers.

The term "mean" as applied herein to a diameter, in certain embodiments, preferably is mass mean. For example, mean physical diameter as used herein, in certain embodiments, preferably is mass mean physical diameter.

The term "comprising" and variations thereof (e.g., comprises, includes, etc.) do not have a limiting meaning where these terms appear in the description and claims.

As used herein, "a," "an," "the," "at least one," and "one or more" are used interchangeably, unless the context clearly dictates otherwise. As used in this specification and the appended claims, the term "or" is generally employed in its sense including "and/or" unless the content clearly dictates otherwise.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the present specification and attached claims are approximations that can vary depending upon the desired properties sought to be obtained by those skilled in the art utilizing the teachings disclosed herein.

Also herein, the recitation of numerical ranges by endpoints includes all numbers subsumed within that range (e.g. 1 to 5 includes 1, 1.5, 2, 2.75, 3, 3.80, 4, and 5; between 1 and 5 includes 1.1, 1.5, 2, 2.75, 3, 3.80, 4, and 4.99) and any range within that range.

The above summary of the present invention is not intended to describe each disclosed embodiment or every implementation of the present invention. The description that follows more particularly exemplifies illustrative embodiments.

DETAILED DESCRIPTION OF ILLUSTRATIVE IMBODIMENTS

Applicants have found that surface-modified nanoparticles can be effectively applied to an active pharmaceutical ingredient by mixing the active ingredient with media particles having surfaces with the surface-modified nanoparticles deposited on the surfaces and then separating the media particles from the active ingredient. In certain embodiments, the mixing is carried out in dry form, with no liquid which could adversely affect the active ingredient or which must be removed by evaporation, sublimation, or the like. The resulting active ingredient is a dry powder with improved flowability and dispersability characteristics. The dry powder can be made part of a dry powder composition with improved flowability and dispersability characteristics. The dry powder or dry powder composition can be used, for example, in an oral solid dosage or an oral inhalation dosage.

When used for oral inhalation, the dry powder or dry powder composition can be used in a dry powder inhaler to deliver the active ingredient to the lung of a mammal. For certain embodiments, preferably the respirable fraction of the dry powder or dry powder composition is increased by at least 20 percent as compared with the same dry powder or dry powder composition without the nanoparticles. For certain of these embodiments, the respirable fraction is increased by at least 30 percent. For certain of these embodiments, the respirable fraction is increased by at least 50 percent or by at least 75 percent.

For certain embodiments, including any one of the above embodiments, preferably active ingredient delivery efficiency for oral inhalation is increased by at least 10 percent using the dry powder or dry powder composition as compared with the same dry powder or dry powder composition without the nanoparticles. For certain of these embodiments, the delivery efficiency is increased by at least 20 percent. For certain of these embodiments, the delivery efficiency is increased by at least 50 percent.

Accordingly, in one embodiment there is provided a method of making active pharmaceutical ingredient particles having surfaces with surface-modified nanoparticles deposited on the surfaces, the method comprising: providing a plurality of media particles having surfaces with surface-modified nanoparticles deposited on the surfaces; mixing the plurality of media particles with active ingredient particles to provide the active ingredient particles having surfaces with a portion of the surface-modified nanoparticles deposited on the surfaces; and separating the plurality of media particles from the active ingredient particles having surfaces with the portion of the surface-modified nanoparticles deposited on the surfaces; wherein the media particles have at least one feature which is sufficiently different from at least one feature of the active ingredient that the media particles can be separated from the active ingredient particles.

Dry powder active ingredient made according to the above method can be used alone or in combination with an inactive ingredient, such as a carrier or other bulking agent. It is believed that when a carrier or other bulking agent is mixed with the active ingredient particles with surface-modified nanoparticles on the particles' surfaces, after mixing the ingredients, some portion of the nanoparticles associated with the active ingredient becomes associated with the surface of the ingredient not previously treated with the nanoparticles. Thus, the resulting dry powder composition has improved characteristics as described above. Such dry powder compositions are described, for example, in copending U.S. Provisional Application Ser. No. 61/075942, filed on Jun. 26, 2008.

For certain embodiments, the method further comprises treating a plurality of media particles with surface-modified nanoparticles to provide the media particles having surfaces with the surface-modified nanoparticles deposited on the surfaces. This can be carried out by mixing the media particles with the surface-modified nanoparticles using a conventional mixing or blending process as long as the nanoparticles are dispersed to the extent that the nanoparticles are not aggregated or, if aggregated, the average diameter of the aggregated particles is less than 100 nm or within any one of the ranges stated herein for the nanoparticles. For certain of these embodiments, treating the plurality of media particles with the surface-modified nanoparticles is carried out by mixing the media particles with the surface-modified nanoparticles in a liquid, and then removing the liquid. For certain of these embodiments, the media particles are substantially insoluble in the liquid, and the surface-modified nanoparticles are dispersible in the liquid. The mixing can be carried out by dispersing the surface-modified nanoparticles in the liquid, adding the media particles to the dispersion, mixing, and removing the liquid.

For certain embodiments, including any one of the above embodiments where the mixing is carried out in a liquid, the liquid is selected from the group consisting of water, an alcohol, a hydrocarbon, a fluorocarbon, a supercritical fluid, and a combination thereof. Alcohols include, for example, ethanol, isopropanol, and the like. Hydrocarbons include hexane, heptane, octane, toluene, and the like. Fluorocarbons include chlorofluorocarbons, such as FREON, hydrofluorocarbons, and perfluorocarbons. Supercritical fluids include carbon dioxide, $C_{1-3}$ hydrocarbons, and the like.

The liquid can be hydrophilic or hydrophobic. When the surface-modified nanoparticles have a hydrophilic surface, the liquid is preferably hydrophilic, for example, the liquid can be water, ethanol, isopropanol, combinations thereof, and the like. When the nanoparticle surface is hydrophobic, the liquid is preferably hydrophobic, for example the liquid can be heptane, hexane, octane, toluene, combinations thereof, or the like.

The liquid can be removed by known processes while avoiding excessive heat that could degrade the media particles or cause melting or dissolving of the media particles. However, media particles can be selected such that the particles are not affected by the chosen conditions where environmental and cost considerations may be important. For certain embodiments, including any one of the above embodiments where the liquid is removed, the liquid is removed by spray drying, rotary evaporation, bulk evaporation, or freeze drying.

Other methods of mixing the media particles with the surface-modified nanoparticles may be used. For example, the mixing may be carried out by blending the nanoparticles with the media particles as powders, i.e., dry blending. For certain embodiments, including any one of the above embodiments other than where a liquid is used, treating the plurality of media particles with the surface-modified nanoparticles is carried out by dry blending the media particles with the surface-modified nanoparticles. Known dry blending processes may be used. However, excessive heat that could degrade the media particles or cause melting of any of the media particles is avoided. Suitable methods include shaking, roll mixing, stirring, tumble mixing, and the like.

In another example, the surface-modified nanoparticles may be dispersed in a liquid as described above, and the resulting dispersion sprayed onto the media particles followed by quickly removing the liquid, for example, by evaporation. Such methods are described in International Application No. PCT/US2009/040892. For certain embodiments, including any one of the above embodiments other than where a liquid or dry blending is used, treating the plurality of media particles with the surface-modified nanoparticles is carried out by spray blending the surface-modified nanoparticles with the media particles; wherein treating the plurality of media particles with surface-modified nanoparticles comprises the step of spraying a liquid dispersion of surface-modified nanoparticles onto the media particles.

Mixing the plurality of media particles with the active ingredient particles to provide active ingredient particles having surfaces with the portion of the surface-modified nanoparticles deposited on the surfaces can be carried out in the presence of an inert liquid, by dry blending, or by other similar methods which brings the media particles in close proximity to the active ingredient particles. When an inert liquid, which does not react with or cause an appreciable change in the media or active ingredient particles, is used the media particles with surface-modified nanoparticles and the active ingredient can be mixed together with the liquid. The media particles can then be separated from the active ingredient particles followed by removal of the liquid, or the liquid can be removed followed by separation of the media particles from the active ingredient particles.

For certain embodiments, including any one of the above embodiments except where a liquid is used, preferably mixing the plurality of media particles with the active ingredient particles to provide active ingredient particles having surfaces with the portion of the surface-modified nanoparticles deposited on the surfaces is carried out by dry blending the plurality of media particles with the active ingredient particles, which are both in dry form. The mixing can be carried out under conditions which facilitate transfer of the portion of the surface-modified nanoparticles from the media particles to the active ingredient particles. Suitable conditions include, for example, shaking, roll mixing, stirring (e.g., in a HOBART mixer), tumble mixing (e.g., in a TURBULA), and the like.

After mixing the media particles with the active ingredient particles, the media particles are separated from the active ingredient particles, which now have the portion of the surface-modified nanoparticles deposited on the particles' surfaces. The separating is based upon the media particles having at least one feature which is sufficiently different from at least one feature of the active ingredient that the media particles can be separated from the active ingredient particles. For certain embodiments, including any one of the above embodiments, the at least one feature is selected from the group consisting of particle diameter, particle aspect ratio, particle density, particle solubility, particle attraction to a magnetic field, particle repulsion from a magnetic field, and a combination thereof. For certain of these embodiments, the at least one feature includes particle diameter, and wherein at least 99 percent by weight of the media particles have a particle diameter at least 10 fold greater than the particle diameter of at least 99 percent by weight of the active ingredient particles. For certain of these embodiment, the at least one feature includes particle diameter, wherein separating the plurality of media particles from the active ingredient particles having surfaces with the portion of the surface-modified nanoparticles deposited on the surfaces comprises sieving the media particles from the active ingredient particles. Air classification can also be used in addition to or instead of sieving to separate the media particles from the active ingredient particles based upon different diameters of these particles. For certain of these embodiments, as an alternative to particle diameter or in addition to particle diameter, the at least one feature includes particle density, wherein at least 99 percent by weight of the media particles have a particle density at least 2 fold greater than the particle density of at least 99 percent by weight of the active ingredient particles. For certain of these embodiments, the at least one feature includes particle density, wherein separating the plurality of media particles from the active ingredient particles having surfaces with the portion of the surface-modified nanoparticles deposited on the surfaces comprises air classifying the media particles from the active ingredient particles. Moreover, air classifying the media particles from the active ingredient particles can be carried out based upon a particle mass difference which can include a particle diameter difference, a particle density difference, or both. For certain of these embodiments, as an alternative to particle diameter and/or particle density, or in addition to particle diameter and/or particle density, the at least one feature includes attraction to a magnetic field, wherein at least 99 percent by weight of the media particles are attracted to the magnetic field, and at least 99 percent by weight of the active ingredient particles are not attracted to the magnetic field. For certain of these embodiments, the at least one feature includes attraction to a magnetic field, wherein separating the plurality of media particles from the active ingredient particles having surfaces with the portion of the surface-modified nanoparticles deposited on the surfaces comprises magnetically attracting the media particles from the active ingredient particles.

The media particles can have any suitable diameter which allows transfer of the surface-modified nanoparticles from the media particles to active ingredient particles, and which is preferably at least 10 fold larger than the diameter of the surface-modified nanoparticles. In certain embodiments, the mean physical diameter is selected so as to reduce interparticle adhesion and, thus, reduce the potential for media particle agglomeration, thereby improving the ability to easily and uniformly blend the media particles with an active ingredient. For certain embodiments, including any one of the above embodiments, the media particles have a mean physical diameter of at least 10 micrometers, at least 50 micrometers, at least 100 micrometers, at least 200 micrometers, or at least 500 micrometers. For certain of these embodiments, the mean physical diameter of the media particles is not more than 5000 micrometers, not more than 2000 micrometers, or not more than 1500 micrometers. For certain of these embodiments, the media particles have a mean physical diameter of 200 micrometers to 5000 micrometers. For certain of these embodiments, the media particles have a mean physical diameter of 200 micrometers to 2000 micrometers. For certain of these embodiments, the media particles have a mean physical diameter of 500 micrometers to 1500 micrometers. Mean physical diameter can be measured by known methods, for example, by laser diffraction or microscopy.

The active ingredient is comprised of particles having a mean physical diameter suitable for use as an oral dosage, an inhalation dosage, or other dosage where flowability of the active ingredient particles during processing and use is advantageous. For certain embodiments, including any one of the above embodiments, the active ingredient particles are micronized. Particles of a micronized ingredient have a mean physical diameter no greater than 100 micrometers. For certain of these embodiments, the active ingredient particles have a mean physical diameter of 1 micrometer to 100 micrometers.

When the active ingredient is to be used as an inhalation dosage, the diameter of the active ingredient particles is relatively small. For certain embodiments, including any one of the above embodiments, preferably the active ingredient is comprised of particles having a mean physical diameter of less than 10 micrometers, more preferably less than 5 micrometers. In certain embodiments, the particles may have a mean physical diameter of between about 1 and 5 micrometers. In one embodiment, the micronized active ingredient may be formed by processes, such as milling, grinding, and high-pressure homogenization, that cause an overall reduction in particle size of larger active ingredient particles. In another embodiment, the micronized active ingredient may, for example, be formed by processes, such as recrystallization, lyophilization, and spray drying, that lead directly to formation of particles of an appropriate particle size. In still another embodiment, the micronized active ingredient may result from controlled agglomeration or aggregation of smaller active ingredient particles. It should be understood that the term "micronized" is used to refer to relatively small particles of the sizes described above and does not suggest that these particles are prepared by any particular process.

The mass median aerodynamic diameter of the micronized active ingredient particles is typically no greater than 100 micrometers. Mass median aerodynamic diameter can be measured by known methods, for example, by laser time of flight or by cascade impactor testing. For certain embodiments, the particles have a mass median aerodynamic diameter which permits the active ingredient to be deposited in the lower lung. For certain embodiments, including any one of the above embodiments, preferably the active ingredient is comprised of particles having a mass median aerodynamic diameter of less than 10 micrometers, more preferably less than 5 micrometers. For certain embodiments, including any one of the above embodiments, the particles have a mass median aerodynamic diameter of at least 1 micrometer and less than 5 micrometers.

When mixing the plurality of media particles with the active ingredient particles, the amount of media particles is sufficient to transfer the portion of surface-modified nanoparticles to the active ingredient particles. The amount of surface-modified nanoparticles transferred is sufficient to improve the flow and/or dispersibility characteristics of the active ingredient particles. For certain embodiments, including any one of the above embodiments, when mixing the plurality of media particles with the active ingredient particles, the active ingredient particles and the media particles are each present in an amount such that the weight ratio of the amount of active ingredient particles to the amount of the media particles is not more than 1:10.

Because, as used in the present methods, the media particles are separated from the active ingredient particles, various materials may be used as the media. However, when mixing particles, for example, in a dry blending process, some fracturing or abrasion of the media particles might potentially occur. For certain embodiments, preferably the media particles are considered to have a low toxicity or to be non-toxic. This may be useful in the event that a small residue of media particle fragments remains with the active ingredient after separating media from active particles.

For certain embodiments, including any one of the above embodiments, preferably the media particles are non-friable. That is, the media particles are sufficiently robust so as not to be physically degraded and leave fragments with the active particles after separation.

For certain embodiments, including any one of the above embodiments, the media particles are selected from the group consisting of inorganic particles, glass beads, ceramic beads, metal beads, for example stainless steel beads, paramagnetic particles, superparamagnetic particles, ferromagnetic particles, ferrimagnetic particles, diamagnetic particles, polymer beads, plastic particles with irregular surfaces, salts, sugars, agate, and a combination thereof. For certain of these embodiments, the media particles are selected from the group consisting of glass beads, ceramic beads, stainless steel beads, superparamagnetic particles, polymer beads, plastic particles with irregular surfaces, salts, sugars, agate, and a combination thereof.

The active ingredient of the present methods can be used for the diagnosis, treatment, cure, prevention, or mitigation of disease. Examples of such active ingredients include but are not limited to medicaments such as antiallergics, analgesics, bronchodilators, antihistamines, therapeutic proteins and peptides, antitussives, anticholinergics, anginal preparations, antibiotics, anti-inflammatory preparations, diuretics, hormones, or sulfonamides, such as, for example, a vasoconstrictive amine, an enzyme, an alkaloid or a steroid, salts thereof, solvates thereof, enantiomers thereof, and combinations of any one or more of these. For certain embodiments, including any one of the above embodiments, the active ingredient is selected from the group consisting of antiallergics, antiasthmatics, antiinflammatories, bronchodilators, steroids, anticholinergics, salts thereof, solvates thereof, enantiomers thereof, and a combination thereof.

Specific examples of active ingredients include isoproterenol, phenylephrine, phenylpropanolamine, glucagon, adrenochrome, trypsin, epinephrine, ephedrine, narcotine, codeine, atropine, heparin, morphine, dihydromorphinone, dihydromorphine, ergotamine, scopolamine, methapyrilene, cyanocobalamin, terbutaline, rimiterol, salbutamol (albuterol), isoprenaline, fenoterol, oxitropium, tiotropium, reproterol, budesonide, flunisolide, ciclesonide, formoterol, fluticasone propionate, salmeterol, procaterol, ipratropium, triamcinolone acetonide, tipredane, mometasone furoate, colchicine, pirbuterol, beclomethasone, beclomethasone dipropionate, orciprenaline, fentanyl, diamorphine, and dilitiazem. Other examples include antibiotics, such as neomycin, cephalosporins, streptomycin, penicillin, procaine penicillin, tetracycline, chlorotetracycline, hydroxytetracycline; adrenocorticotropic hormone and adrenocortical hormones, such as cortisone, hydrocortisone, hydrocortisone acetate and prednisolone; antiallergy compounds such as cromolyn sodium and nedocromil; protein and peptide molecules such as insulin, pentamidine, calcitonin, amiloride, interferon, LHRH analogues, IDNAase, heparin, and others.

For certain embodiments, including any one of the above embodiments, the active ingredient is selected from the group consisting of budesonide, albuterol, formoterol, fluticasone, salmeterol, mometasone, tiotropium, beclomethasone, salts thereof, solvates thereof, enantiomers thereof, and a combination thereof.

For a specific application the active ingredient (drug or medicament) may be used as either a free base or as one or more salts thereof. The choice of a free base or salt will be influenced by the biological impact as well as the chemical and physical stability (e.g., its tendency toward solvates, multiple polymorphs, friability, etc.) of the active ingredient in a given formulation. Examples of anionic salts of active ingredients that may be used in the present compositions include acetate, benzenesulphonate, benzoate, bicarbonate, bitartrate, bromide, calcium edetate, camsylate, carbonate, chloride, citrate, dihydrochloride, edetate, edisylate, estolate, esylate, fumarate, fluceptate, gluconate, glutamate, glycollylarsanilate, hexylresorcinate, hydrobromide, hydrochloride, hydroxynaphthoate, iodide, isethionate, lactate, lactobionate, malate, maleate, mandelate, mesylate, methylbromide, methylnitrate, methylsulphate, mucate, napsylate, nitrate, pamoate (embonate), pantothenate, phosphate-diphosphate, polygalacturonate, salicylate, stearate, subacetate, succinate, sulphate, tannate, tartrate, and triethiodide.

Examples of cationic salts of an active ingredient that may be used in the present methods include alkali metals, e.g., sodium and potassium; and ammonium salts and salts of amines known in the art to be pharmaceutically acceptable, e.g., glycine, ethylene diamine, choline, diethanolamine, triethanolamine, octadecylamine, diethylamine, triethylamine, 1-amino-2-propanol, 2-amino-2-(hydroxymethyl)propane-1,3-diol, and 1-(3,4-dihydroxyphenyl)-2-isopropylaminoethanol.

The surface-modified nanoparticles used in the present methods are comprised of a core material and a surface that is different (i.e., modified) from the core material. The core material may be inorganic or organic and is selected such that it is compatible with the active ingredient and with the media particles and suitable for the application for which the active ingredient or a dry powder composition containing the active ingredient is intended. The selection of the core material will also be governed at least in part by specific performance requirements for the composition. For example, the performance requirements for the composition might require that a given core material have certain dimensional characteristics (e.g., size and shape), compatibility with the surface modifying materials along with certain stability requirements (e.g., insolubility in a processing or mixing liquid, good dispersibility in a processing or mixing liquid). Requirements can include, for example, biocompatibility, biosolubility, biodegradability, and stability under more extreme environments (e.g., higher temperatures during processing or shipping, resistance to moisture uptake) as well as the ability to dry the surface-modified nanoparticles down to a powder and subsequently maintain the ability to re-disperse the nanoparticles in a processing or mixing liquid.

Suitable inorganic nanoparticle core materials include metal oxide nanoparticles such as silica, titania, alumina, iron oxide, zinc oxide, antimony oxide, tin oxide, alumina/silica, ceria, vanadia, metal phosphates, e.g., calcium phosphates including hydroxyapatite, metal sulfates, metal chlorides, and combinations thereof. For certain embodiments, including any one of the above embodiments, the surface-modified nanoparticles comprise a core, the core comprising an inorganic material selected from the group consisting of silica, titania, alumina, an oxide of zinc, an oxide of iron, metal phosphates, metal sulfates, metal chlorides, or a combination thereof. Metals such as gold, silver, or other precious metals can also be utilized as solid particles or as coatings on organic or inorganic particles.

Suitable organic nanoparticle core materials include, for example, organic polymeric nanospheres, sugars such as lactose, trehalose, glucose or sucrose, and aminoacids. For certain embodiments, including any one of the above embodiments except where the core material is inorganic, the surface-modified nanoparticles comprise a core, the core comprising an organic polymer. For certain of these embodiments, the core comprises polystyrene. Organic polymeric nanospheres are known and include nanospheres that comprise polystyrene, such as those available from Bangs Laboratories, Inc. of Fishers, Ind. as powders or dispersions. Such organic polymeric nanospheres will generally have average particle sizes ranging from 20 nm to not more than 60 nm.

A selected nanoparticle core material may be used alone or in combination with one or more other nanoparticle core materials including mixtures and combinations of organic and inorganic nanoparticle materials. Such combinations may be uniform or have distinct phases which can be dispersed or regionally specific, e.g., layered or of a core-shell type structure.

The nanoparticle core, whether inorganic or organic, and in whatever form employed, will have a mean particle diameter of less than 100 nm. For certain embodiments, the nanoparticles have a mean particle diameter of not more than 50 nm, preferably not more than 20 nm; in certain embodiments from 2 nm to 20 nm; and in certain other embodiments from 3 nm to 10 nm or more preferably from 4 nm to 8 nm. If the chosen nanoparticle or combination of nanoparticles are themselves aggregated, the maximum preferred cross-sectional dimension of the aggregated particles will be within any one of these stated ranges.

In an exemplary embodiment, another class of surface-modified organic nanoparticles includes buckminsterfullerenes (fullerenes), dendrimers, branched and hyperbranched "star" polymers such as 4, 6, or 8 armed polyethylene oxides (available, for example, from Aldrich Chemical Company of Milwaukee, Wis. or Shearwater Corporation of Huntsville, Ala.) whose surfaces have been chemically modified. Specific examples of fullerenes include $C_{60}$, $C_{70}$, $C_{82}$, and $C_{84}$. Specific examples of dendrimers include polyamidoamine (PAMAM) dendrimers of Generations 2 through 10 (G2-G10), available also from, for example, Aldrich Chemical Company of Milwaukee, Wis.

In many cases it may be desirable for the nanoparticles utilized in the invention to be substantially spherical in shape. In other applications, however, more elongated shapes may be desired. Aspect ratios of not more than 10 are preferred, with aspect ratios not more than 3 generally more preferred. The core material will substantially determine the final morphology of the particle and thus a significant influence in selection of the core material may be the ability to obtain a desired size and shape in the final particle.

The surface of the selected nanoparticle core material will generally be chemically or physically modified in some manner. Both direct modification of a core surface as well as modification of a permanent or temporary shell on a core material are envisioned. Such modifications may include, for example, covalent chemical bonding, hydrogen bonding, electrostatic attraction, London forces, and hydrophilic or hydrophobic interactions so long as the interaction is maintained at least during the time period required for the nanoparticles to achieve their intended utility. The surface of a nanoparticle core material may be modified with one or more surface modifying groups. The surface modifying groups may be derived from various surface modifying agents. Schematically, surface modifying agents may be represented by the following general formula:

$$A-B \qquad (II)$$

The A group in Formula II is a linking group that is capable of attaching to the surface of the nanoparticle. In those situations where the nanoparticles and the media particles are processed in a liquid, the B group is a compatibilizing group with the liquid. The B group may also be a group or moiety that is capable of preventing irreversible agglomeration of the nanoparticles. It is possible for the A and B groups to be the same, e.g., the attaching group may also be capable of providing the desired surface compatibility. The compatibilizing group may be reactive, but is generally non-reactive, with a component of the media particles or the active ingredient. The A group may be comprised of more than one component or created in more than one step, e.g., the A group may be comprised of an A' moiety which is reacted with the surface, and an A" moiety which can be reacted with B. The sequence of these reactions is not important, as these reactions can be wholly or partly performed prior to the attachment to the core. Further description of nanoparticles in coatings can be found in Linsenbuhler, M. et. al., *Powder Technology*, 158, 2003, p. 3-20.

Many suitable classes of surface-modifying compounds are known to those skilled in the art and include, for example, silanes, organic acids, organic bases, inorganic acids with organic groups, and alcohols, and combinations thereof. For certain embodiments, including any one of the above embodiments, a surface of the core is modified with a compound selected from the group consisting of alkylsilanes, carboxylic acids, phosphonic acids, sulfonates, polyethylene glycols, sugars, and a combination thereof.

For certain embodiments, the surface-modifying compound is a silane. Examples of silanes include organosilanes such as, for example, alkylchlorosilanes, alkoxysilanes, e.g., methyltrimethoxysilane, methyltriethoxysilane, ethyltrimethoxysilane, ethyltriethoxysilane, n-propyltrimethoxysilane, n-propyltriethoxysilane, isopropyltrimethoxysilane, isopropyltriethoxysilane, butyltrimethoxysilane, butyltriethoxysilane, hexyltrimethoxysilane, octyltrimethoxysilane, 3-mercaptopropyltrimethoxysilane, n-octyltriethoxysilane, phenyltriethoxysilane, polytriethoxysilane, vinyltrimethoxysilane, vinyldimethylethoxysilane, vinylmethyldiacetoxysilane, vinylmethyldiethoxysilane, vinyltriacetoxysilane, vinyltriethoxysilane, vinyltriisopropoxysilane, vinyltrimethoxysilane, vinyltriphenoxysilane, vinyltri(t-butoxy)silane, vinyltris(isobutoxy)silane, vinyltris(isopropenoxy)silane, and vinyltris(2-methoxyethoxy)silane; trialkoxyarylsilanes; isooctyltrimethoxy-silane; N-(3-triethoxysilylpropyl) methoxyethoxyethoxy ethyl carbamate; N-(3-triethoxysilylpropyl) methoxyethoxyethoxyethyl carbamate; silane functional (meth)acrylates including, e.g., 3-(methacryloyloxy)propyltrimethoxysilane, 3-acryloyloxypropyltrimethoxysilane, 3-(methacryloyloxy)propyltriethoxysilane, 3-(methacryloyloxy)propylmethyldimethoxysilane, 3-(acryloyloxypropyl)methyldimethoxysilane, 3-(methacryloyloxy)propyldimethylethoxysilane, 3-(methacryloyloxy)methyltriethoxysilane, 3-(methacryloyloxy)methyltrimethoxysilane, 3-(methacryloyloxy)propyldimethylethoxysilane, 3-(methacryloyloxy)propenyltrimethoxysilane, and 3-(methacryloyloxy)propyltrimethoxysilane; polydialkylsiloxanes including, e.g., polydimethylsiloxane, arylsilanes including, e.g., substituted and unsubstituted arylsilanes, alkylsilanes including, e.g., substituted and unsubstituted alkyl silanes including, e.g., methoxy and hydroxy substituted alkyl silanes, and combinations thereof.

Methods of surface-modifying silica using silane functional (meth)acrylates are known and are described, for example, in U.S. Pat. No. 4,491,508 (Olson et al.); U.S. Pat. No. 4,455,205 (Olson et al.); U.S. Pat. No. 4,478,876 (Chung); U.S. Pat. No. 4,486,504 (Chung); and U.S. Pat. No. 5,258,225 (Katsamberis) whose descriptions are incorporated herein by reference for such purpose. Surface-modified silica nanoparticles include silica nanoparticles surface-modified with silane surface modifying agents including, for example, acryloyloxypropyl trimethoxysilane, 3-methacryloyloxypropyltrimethoxysilane, 3-mercaptopropyltrimethoxysilane, n-octyltrimethoxysilane, isooctyltrimethoxysilane, and combinations thereof. Silica nanoparticles can be treated with a number of surface modifying agents including, for example, an alcohol, an organosilane including, for example, alkyltrichlorosilanes, trialkoxyarylsilanes, trialkoxy(alkyl)silanes, and combinations thereof, and organotitanates, and mixtures thereof.

In another embodiment, the surface-modifying compound is an organic acid or an inorganic acid with an organic group. Examples of such compounds include oxyacids of carbon (e.g., carboxylic acid), sulfur and phosphorus, acid derivatized poly(ethylene glycols) (PEGs) and combinations of any of these. Suitable phosphorus containing acids include phosphonic acids including, for example, octylphosphonic acid, laurylphosphonic acid, decylphosphonic acid, dodecylphosphonic acid, octadecylphosphonic acid, monopolyethylene glycol phosphonate and phosphates including lauryl or stearyl phosphate. Suitable sulfur containing acids include sulfates and sulfonic acids including dodecyl sulfate and lauryl sulfonate. Any such acids may be used in either acid or salt forms.

Other surface modifying compounds with carboxyl groups include acrylic acid, methacrylic acid, beta-carboxyethyl acrylate, mono-2-(methacryloyloxyethyl) succinate, mono(methacryloyloxypolyethyleneglycol) succinate and combinations of one or more of such compounds. For certain embodiments, surface-modifying agents which incorporate a carboxylic acid functionality include, for example, $CH_3O(CH_2CH_2O)_2CH_2COOH$ (hereafter MEEAA), 2-(2-methoxyethoxy)acetic acid having the chemical structure $CH_3OCH_2CH_2OCH_2COOH$ (hereafter MEAA), mono(polyethylene glycol) succinate in either acid or salt form, octanoic acid, dodecanoic acid, steric acid, acrylic and oleic acid or their acidic derivatives. In a further embodiment, surface-modified iron oxide nanoparticles include those modified with endogenous fatty acids, e.g., steric acid, or fatty acid deriviatives using endogenous compounds, e.g., steroyl lactylate or sarcosine or taurine derivatives.

In another embodiment, the surface-modifying compound is an organic base. Examples of such compounds include alkylamines, e.g., octylamine, decylamine, dodecylamine, octadecylamine, and monopolyethylene glycol amines.

In another embodiment, the surface-modifying compound is an alcohol or thiol. Examples of such compounds include, for example, aliphatic alcohols, e.g., octadecyl, dodecyl, lauryl and furfuryl alcohol, alicyclic alcohols, e.g., cyclohexanol, and aromatic alcohols, e.g., phenol and benzyl alcohol, and combinations thereof. Thiol-based compounds are especially suitable for modifying cores with gold surfaces.

The surface-modified nanoparticles are selected in such a way that compositions formed with them are free from a degree of particle agglomeration or aggregation that would interfere with the desired properties of the composition. The surface-modified nanoparticles are generally selected to be either hydrophobic or hydrophilic such that, depending on the character of the processing liquid, the media particles, and/or the active ingredient, the resulting treated media particles and active ingredient particles exhibit substantially free flowing properties. Suitable surface groups constituting the surface modification of the utilized nanoparticles can thus be selected based upon these considerations. When a processing liquid is hydrophobic, for example, one skilled in the art can select from among various hydrophobic surface groups to achieve a surface-modified particle that is compatible with the hydrophobic liquid; when the processing liquid is hydrophilic, one skilled in the art can select from various hydrophilic surface groups; and, when the solvent is a hydrofluorocarbon, one skilled in the art can select from among various compatible surface groups; and so forth. The nanoparticle can include two or more different surface groups (e.g., a combination of hydrophilic and hydrophobic groups) that combine to provide a nanoparticle having a desired set of characteristics. The surface groups will generally be selected to provide a statistically averaged, randomly surface-modified nanoparticle.

The surface groups will be present on the surface of the nanoparticle in an amount sufficient to provide surface-modified nanoparticles with the properties necessary for compatibility with processing liquid, the active ingredient, or the media particles. In an exemplary embodiment, the surface groups are present in an amount sufficient to form a monolayer, and in another embodiment, a continuous monolayer, on at least a substantial portion of the surface of the nanoparticle.

A variety of methods are available for modifying the surfaces of nanoparticles. A surface modifying agent may, for example, be added to nanoparticles (e.g., in the form of a powder or a colloidal dispersion) and the surface modifying agent may be allowed to react with the nanoparticles. One skilled in the art will recognize that multiple synthetic sequences to bring the nanoparticle together with the compatibilizing group are known and can be used. For example, the reactive group/linker may be reacted with the nanoparticle followed by reaction with the compatibilizing group. Alternatively, the reactive group/linker may be reacted with the compatibilizing group followed by reaction with the nanoparticle. Other surface modification processes are described in, e g., U.S. Pat. No. 2,801,185 (Iler) and U.S. Pat. No. 4,522,958 (Das et al.), whose descriptions are incorporated herein by reference for such purpose.

Surface-modified nanoparticles or precursors to them may be in the form of a colloidal dispersion. Some such dispersions are commercially available as unmodified silica starting materials, for example those nano-sized colloidal silicas available under the product designations NALCO 1040, 1050, 1060, 2326, 2327, and 2329 colloidal silica from Nalco Chemical Co. of Naperville, Ill. Metal oxide colloidal dispersions include colloidal titanium oxide, examples of which are described in U.S. Pat. Nos. 6,329,058 and 6,432,526 (Arney et al.), whose descriptions are also incorporated by reference herein. Such particles are also suitable substrates for further surface modification as described above.

For certain embodiments, including any one of the above embodiments, the surface-modified nanoparticles have a mean particle diameter of not more than 50 nm.

For certain of these embodiments, the surface-modified nanoparticles have a mean diameter of not more than 20 nanometers. For certain of these embodiments, the surface-modified nanoparticles have a mean diameter of 2 nm to 20 nm; and in certain other embodiments from 3 nm to 10 nm or more preferably from 4 nm to 8 nm. If the chosen surface-modified nanoparticle or combination of surface-modified nanoparticles are themselves aggregated, the maximum preferred cross-sectional dimension of the aggregated surface-modified nanoparticles will be within any one of these stated ranges.

The surface-modified nanoparticles are present with the active ingredient, after separation from the media particles, in an amount effective to enhance a property which is relevant to processing or delivering the active ingredient. For example, the degree of aggregation, agglomeration or flocculation of the active ingredient can be reduced or minimized by the surface-modified nanoparticles. The amount of surface-modified nanoparticles effective to achieve such purposes will depend, inter alia, on the chosen nanoparticle, the presence or absence of other adjuvants or excipients added to the active ingredient, and on the particular needs and requirements of the application for which the active ingredient is to be used. For example, the nature of the nanoparticle surface, the morphology of the particle and particle size may each influence the desired properties of the active ingredient or composition in which the active ingredient is placed and influence the selection of a nanoparticle and the amount or concentration of nanoparticles used. The presence of as little as 0.0001 percent of nanoparticles by weight of the active ingredient may provide a desired effect. For certain embodiments, the amount of surface-modified nanoparticles is at least 0.01 weight percent. The surface-modified nanoparticles may be used in an amount not exceeding 10 weight percent, and in certain embodiments in an amount not more than 5 weight percent of the active ingredient. For certain embodiments, including any one of the above embodiments, the amount of surface-modified nanoparticles with the active ingredient is at least 0.02 percent and not more than 5 percent by weight of the active ingredient. For certain of these embodiments, the amount of surface-modified nanoparticles with the active ingredient is 0.1 to 3 weight percent of the active ingredient.

In certain applications it may be preferred that the selected nanoparticles be substantially spherical. The biocompatibility, including toxicology, and physical properties of a selected surface-modified nanoparticle is considered according to the skill in the art for the present method or dry powder compositions containing active ingredient resulting from the method in accordance with the contemplated use or application.

In one exemplary embodiment, the surface-modified nanoparticles will not irreversibly associate with one another. The term "associate with" or "associating with" includes, for example, covalent bonding, hydrogen bonding, electrostatic attraction, London forces, and hydrophobic interactions.

The surface-modified nanoparticles used in the present methods as described above can in certain embodiments provide a significant increase in delivery efficiency of an active ingredient, a significant increase in respirable fraction, or both.

The surface-modified nanoparticles utilized in the methods described herein typically enhance and/or maintain the flowability of the active ingredient particles and/or a dry powder composition comprising the active ingredient particles with surface-modified nanoparticles. Flowability (also called free flow) refers generally to the ability of a free-flowing material to flow steadily and consistently as individual particles or groups of individual particles such as would occur, for example, through a fine orifice. Relative improvements (i.e., reductions) in aggregation, agglomeration, attrition, flocculation, segregation, caking, bridging or in the ability to achieve uniform blends indicate an improvement in flowability.

The presence of nanoparticles as provided in the present methods can also enhance floodability (also called floodable flow), which refers to the tendency of a solid or powder material toward liquid-like flow due to the material fluidization of a mass of particles by a gaseous carrier.

Also, the presence of the surface-modified nanoparticles may allow for higher tap densities, where a larger concentration of the active ingredient particles or a dry powder composition containing the active ingredient particles may be contained in a capsule, a blister, or a reservoir-based DPI device. For example, this may contribute to more doses in a DPI device within the same sized device, rather than changing the device's shape or size.

Objects and advantages of this invention are further illustrated by the following examples, but the particular materials and amounts thereof recited in these examples, as well as other conditions and details, should not be construed to limit the scope of the present invention.

EXAMPLES

Unless otherwise indicated, all parts and percentages are by weight.

Silica SMN Dispersion Preparation

Hydrophobic silica surface-modified nanoparticles (SMN) were prepared by mixing 600 grams of Nalco 2326 colloidal silica, 56.8 grams of isooctyltrimethoxysilane (Gelest, Inc.), 540 grams of ethanol, and 135 grams of methanol in a 2 liter flask at approximately 82° C. for 4 hours. The resulting white particulate product was isolated and oven dried at 120° C.

A surface-modified nanoparticle dispersion was prepared by adding 5.0414 grams of the hydrophobic silica SMN to 500 mL of heptane and stirring until the SMN had completely dispersed. The resulting SMN-heptane dispersion had a nominal concentration of 0.0101 g/mL.

Example 1

An amount of 100.0 grams of spherical glass media (A-100, 0.8 to 1.2 mm size, soda-lime silica glass, density=2.5 g/cm$^3$, available from Potters Industries Inc., Valley Forge, Pa.) was added to a 500 mL round bottom flask. An aliquot of 100 mL of the Silica SMN dispersion preparation was added to the flask. The mixture was then sonicated and swirled for approximately 15 seconds to ensure uniform mixture in the flask. The flask was then placed onto a rotary evaporator to remove the liquid (heptane). The rotary evaporator was set to a nominal temperature of 60° C. and operated under a vacuum. After removal of all of the visible liquid, the flask was then placed into a vacuum oven at approximately 45° C. for approximately 1 hour to remove further residual liquid, thus providing glass media coated with surface-modified nanoparticles.

A 50.0 g portion of the glass media coated with surface-modified nanoparticles and 2.0008 g micronized albuterol base (particle size: d10=0.7 μm, d50=1.9 μm, d90=3.8 μm, Cambrex Profarmaco Milano S.r.l., Milan Italy) were added to a 4 oz (118 mL) glass jar. The jar was shaken for approximately 5 minutes during which time it was occasionally opened to loosen any powder that was sticking to the jar surface. The mixture was sieved with a No. 70 mesh sieve (210 micron opening) to separate the glass media from the albuterol powder. The resulting, treated albuterol powder had significantly improved flow and dispersibility compared to the untreated albuterol powder. Scanning electron microscope observation confirmed that the treated albuterol was partially coated with surface-modified nanoparticles.

Example 2

An amount of 100.0 grams of spherical glass media (A-100, 0.8 to 1.2 mm size, soda-lime silica glass, density=2.5 g/cm$^3$, available from Potters Industries Inc., Valley Forge, Pa.) was added to a 500 mL round bottom flask. An aliquot of 50 mL of the Silica SMN dispersion preparation was diluted with an additional 50 mL of heptane and this dispersion was then added to the flask. The mixture was then sonicated and swirled for approximately 15 seconds to ensure uniform mixture in the flask. The flask was then placed onto a rotary evaporator to remove the liquid (heptane). The rotary evaporator was set to a nominal temperature of 60° C. and operated under a vacuum. After removal of all of the visible liquid, the flask was then placed into a vacuum oven at approximately 45° C. for approximately 1 hour to remove further residual liquid, thus providing glass media coated with surface-modified nanoparticles.

A 50.0 g portion of the glass media coated with surface-modified nanoparticles and 2.0055 g micronized albuterol base (particle size: d10=0.7 μm, d50=1.9 μm, d90=3.8 μm, Cambrex Profarmaco Milano S.r.l., Milan Italy) were added to a 4 oz (118 mL) glass jar. The jar was shaken for approximately 5 minutes during which time it was occasionally opened to loosen any powder that was sticking to the jar surface. The mixture was sieved with a No. 70 mesh sieve (210 micron opening) to separate the glass media from the albuterol powder. The resulting, treated albuterol powder had improved flow and dispersibility compared to the untreated albuterol powder. Scanning electron microscope observation confirmed that the treated albuterol was partially coated with surface-modified nanoparticles.

Example 3

An amount of 100.0 grams of spherical glass media (A-100, 0.8 to 1.2 mm size, soda-lime silica glass, density=2.5 g/cm$^3$, available from Potters Industries Inc., Valley Forge, Pa.) was added to a 500 mL round bottom flask. An aliquot of 25 mL of the Silica SMN dispersion preparation was diluted with an additional 75 mL of heptane and this dispersion was then added to the flask. The mixture was then sonicated and swirled for approximately 15 seconds to ensure uniform mixture in the flask. The flask was then placed onto a rotary evaporator to remove the liquid (heptane). The rotary evaporator was set to a nominal temperature of 60° C. and operated under a vacuum. After removal of all of the visible liquid, the flask was then placed into a vacuum oven at approximately 45° C. for approximately 1 hour to remove further residual liquid, thus providing glass media coated with surface-modified nanoparticles.

A 50.0 g portion of the glass media coated with surface-modified nanoparticles and 2.0114 g micronized albuterol base (particle size: d10=0.7 μm, d50=1.9 μm, d90=3.8 μm, Cambrex Profarmaco Milano S.r.l., Milan Italy) were added to a 4 oz (118 mL) glass jar. The jar was shaken for approximately 5 minutes during which time it was occasionally opened to loosen any powder that was sticking to the jar surface. The mixture was sieved with a No. 70 mesh sieve (210 micron opening) to separate the glass media from the albuterol powder. The resulting, treated albuterol powder had modestly improved flow and dispersibility compared to the untreated albuterol powder. Scanning electron microscope observation confirmed that the treated albuterol was partially coated with surface-modified nanoparticles.

Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein.

The complete disclosures of the patents, patent documents, and publications cited herein are incorporated by reference in their entirety or the portions of each that are indicated as if each were individually incorporated.

What is claimed is:

1. A method of making active pharmaceutical ingredient particles having surfaces with surface-modified nanoparticles deposited thereon, the method comprising:

providing a plurality of media particles having surfaces with surface-modified nanoparticles deposited on the surfaces of the media particles;

mixing the plurality of media particles with active ingredient particles to transfer surface-modified nanoparticles from the media particles to the active ingredient particles and provide active ingredient particles having surfaces with a portion of the surface-modified nanoparticles deposited thereon; and subsequently, separating the plurality of media particles from the active ingredient particles having surfaces with the portion of the surface-modified nanoparticles deposited thereon;

wherein the media particles have at least one feature which is different from at least one feature of the active ingredient such that the media particles can be separated from the active ingredient particles.

2. The method of claim 1, further comprising treating a plurality of media particles with surface-modified nanoparticles to provide the media particles having surfaces with the surface-modified nanoparticles deposited on the surfaces.

3. The method of claim 2, wherein treating the plurality of media particles with the surface-modified nanoparticles is carried out by mixing the media particles with the surface-modified nanoparticles in a liquid, and then removing the liquid; and wherein the media particles are substantially insoluble in the liquid, and the surface-modified nanoparticles are dispersible in the liquid.

4. The method of claim 3, wherein the liquid is selected from the group consisting of water, an alcohol, a hydrocarbon, a fluorocarbon, a supercritical fluid, and a combination thereof.

5. The method of claim 3, wherein the liquid is removed by rotary evaporation, bulk evaporation, spray drying, or freeze drying.

6. The method of claim 2, wherein treating the plurality of media particles with the surface-modified nanoparticles is carried out by dry blending the media particles with the surface-modified nanoparticles.

7. The method of claim 2, wherein treating the plurality of media particles with surface-modified nanoparticles comprises the step of spraying a liquid dispersion of surface-modified nanoparticles onto the media particles.

8. The method of claim 1, wherein mixing the plurality of media particles with the active ingredient particles to provide active ingredient particles having surfaces with the portion of the surface-modified nanoparticles deposited on the surfaces of the active pharmaceutical ingredient particles is carried out by dry blending the plurality of media particles with the active ingredient particles, which are both in dry form.

9. The method of claim 1, wherein the at least one feature is selected from the group consisting of particle diameter, particle aspect ratio, particle density, particle solubility, particle attraction to a magnetic field, particle repulsion from a magnetic field, and a combination thereof.

10. The method of claim 9, wherein the at least one feature includes particle diameter, and wherein at least 99 percent by weight of the media particles have a particle diameter at least 10 fold greater than the particle diameter of at least 99 percent by weight of the active ingredient particles.

11. The method of claim 9, wherein the at least one feature includes particle density, wherein at least 99 percent by weight of the media particles have a particle density at least 2 fold greater than the particle density of at least 99 percent by weight of the active ingredient particles.

12. The method of claim 1, wherein the media particles have a mean physical diameter of 200 micrometers to 5000 micrometers.

13. The method of claim 1, wherein the active ingredient particles are micronized.

14. The method of claim 1, wherein the active ingredient particles have a mass median aerodynamic diameter of at least 1 micrometer and less than 5 micrometers.

15. The method of claim 1, wherein when mixing the plurality of media particles with the active ingredient particles, the active ingredient particles and the media particles are each present in an amount such that the weight ratio of the amount of active ingredient particles to the amount of the media particles is not more than 1:10.

16. The method of claim 1, wherein the media particles are non-friable.

17. The method of claim 1, wherein the surface-modified nanoparticles comprise a core, the core comprising an organic core or an inorganic material selected from the group consisting of silica, titania, alumina, an oxide of zinc, an oxide of iron, metal phosphates, metal sulfates, metal chlorides, or a combination thereof.

18. The method of claim 17, wherein a surface of the core is modified with a compound selected from the group consisting of alkylsilanes, carboxylic acids, phosphonic acids, sulfonates, polyethylene glycols, sugars, and a combination thereof.

19. The method of claim 1, wherein the surface-modified nanoparticles have a mean diameter of not more than 20 nanometers.

20. The method of claim 1, wherein the surface-modified nanoparticles deposited on the surfaces of the media particles are present in an amount of at least 0.1 percent and not more than 10 percent by weight of the media particles.

\* \* \* \* \*